United States Patent [19]

Johnson et al.

[11] Patent Number: 5,359,110
[45] Date of Patent: Oct. 25, 1994

[54] PROCESS FOR THE PREPARATION OF A R-ALPHA CYCLOPENTENONES AND R-ALPHA AND R-OMEGA CYCLOPENTANOIDS

[75] Inventors: Carl R. Johnson, Detroit, Mich.; Matthew P. Braun, Sandusky, Ohio

[73] Assignee: Board of Governors of Wayne State University, Detroit, Mich.

[21] Appl. No.: 155,589

[22] Filed: Nov. 16, 1993

[51] Int. Cl.$^5$ ................................ C07F 7/08
[52] U.S. Cl. .................................... 556/436
[58] Field of Search .......................... 56/436

[56] References Cited

U.S. PATENT DOCUMENTS 4,873,360 10/1989 Johnson et al. .............. 560/121
5,136,066 8/1992 Takahashi et al. ............ 556/436
5,180,844 1/1993 Takahashi et al. ............ 556/436
5,254,708 10/1993 Sato et al. ................... 556/436

OTHER PUBLICATIONS

Collins, P. W., et al., Chem. Rev. 93, 1533 (1993).
Corey, E. J., et al., J. Am. Chem. Soc., 91, 5675 (1969).
Noyori, R., et al. Angew. Chem., Int. Ed. Engl., 23, 847 (1984).
Noyori, R., et al., J. Am. Chem. Soc. 110, 4718 (1988).
Noyori, R., et al., Chemtracts: Org. Chem., 173 (1990).
Johnson, C. R., et al., J. Am. Chem. Soc. 110, 4726 (1988).
Sih, C. J., et al., J. Am. Chem. Soc. 94, 3643 (1972).
Sato, F., et al., Tetrahedron Lett., 31, 4481 (1990).
Gooding, O. W., et al., J. Org. Chem. 58, 3681 (1993).
Morita, Y., et al., J. Org. Chem., 54, 1785 (1989).
Babiak, K. A., et al., J. Org. Chem. 55, 3377 (1990).
Sato, F., et al., J. Org. Chem., 53 5590 (1988).
Johnson, C. R., et al., Tetrahedron Lett., 33, 917 (1992).

Miyaura, N., et al., M. Am. Chem. Soc. 111, 314–321 (1989).
Suzuki, A., et al, Pure & Appl. Chem., 63, 419 (1991).
Hayashi, T., et al., J. Am. Chem. Soc., 106, 158 (1984).
Johnson, C. R., Tetrahedron Lett., 33, 7287 (1992).
Sih, C. J., et al., J. Am. Chem. Soc., 97, 865 (1975).
Griengl, H., et al., Tetrahedron, 43, 5791 (1987).
Corey, E. J., et al., Tetrahedron Lett., 27, 2199 (1986).
Farina, V., et al., J. Am. Chem. Soc. 113, 9585 (1991).
Campbell, A. L., et al., J. Am. Chem. Soc., 110, 2641 (1988).
Myers, A. G., et al., J. Am. Chem. Soc. 115, 7021 (1993).

*Primary Examiner*—Paul F. Shaver
*Attorney, Agent, or Firm*—Ian C. McLeod

[57] ABSTRACT

A process for the preparation of R$\alpha$-cyclopentenoids and then R$\alpha$, R$\omega$-cyclopentanoids is described. The process involves the reaction of a compound of the formula

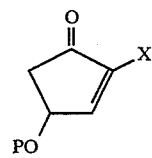

where X is halo, particularly Br or I and P is a protecting group with an alkylborane to produce the R$\alpha$-cyclopentenone. The R$\alpha$-cyclopentenone is reacted with a R$\omega$ cuprate to produce the R$\alpha$, R$\omega$-cyclopentenoid. The process is used for the preparation of prostaglandins which are known pharmaceutically active compounds.

12 Claims, No Drawings

PROCESS FOR THE PREPARATION OF A R-ALPHA CYCLOPENTENONES AND R-ALPHA AND R-OMEGA CYCLOPENTANOIDS

This invention was made with Government support, under Contract No. CHE 92 23001, awarded by the National Science Foundation. The Government has certain rights in the invention.

BACKGROUND OF THE INVENTION (1) Field of the Invention

The present invention relates to a process for the preparation of Rα-cyclopentenones and thereafter Rα, Rω-cyclopentanoids, particularly prostaglandins (PGs). The process involves the reaction of a protected 4-hydroxy α-iodo or α-bromoenone with an alkylborane to produce the Rα-cyclopentenone. The Rα-cyclopentenone is reacted with a cuprate or other Rα-organometallics to provide a cyclopentanoid of the formula:

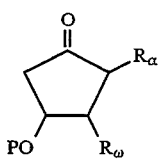

P is a protecting group which is removed by conventional methods to provide the 4-hydroxy group.

(2) Background of the Invention

General and efficient syntheses of prostaglandins (PGs) have been the subject of much effort over the past three decades (Collins, P. W., et al., Chem. Rev. 93, 1533 (1993)). Aside from the widely applied, but lengthy, Corey synthesis (Corey, E. J., et al., J. Am. Chem. Soc., 91, 5675 (1969)), two other popular approaches have emerged from these efforts: the three-component coupling process (Noyori, R., et al. Angew. Chem., Int. Ed. Engl., 23, 847 (1984); and Noyori, R., et al., J. Am. Chem. Soc. 110, 4718 (1988); Noyori, R., et al, Chemtracts: Org. Chem., 173 (1990); and Johnson, C. R., et al., J. Am. Chem. Soc. 110, 4726 (1988)) and the two-component (conjugate addition) process (Sih, C. J., et al., J. Am. Chem. Soc. 94, 3643 (1972); and Sato, F., et al., Tetrahedron Lett., 31, 4481 (1990)).

PGs. The use of (R)-4-(tert-butyldimethylsiloxy)-2-cyclopentenone (compound 1a) as an enantiopure component in this process is a particular advantage due to its ease of preparation (Noyori, R., et al., J. Am. Chem. Soc., 110, 4718 (1988)). Despite the attractiveness of this approach and the improvements which have been made upon it, (Gooding, O. W., et al., J. Org. Chem. 58, 3681 (1993); and Morita, Y., et al., J. Org. Chem., 54, 1785 (1989)), several limitations still exist. Most important are the problems of enolate equilibrium and β-alkoxide elimination associated with alkylation of the intermediate enolate, problems which are especially evident when trapping with unactivated electrophiles such as a halide corresponding to the α-chain of $PGE_1$. As a result, the two component synthesis (conjugate addition of Rω to a 4(R)-alkoxy-2-alkyl-2-cyclopentenone, Equation 2 has remained a highly studied and valuable route to PGs. The limiting factor of this approach has been the availability of the enantiopure αalkylcyclopentenones (compound 2) (Babiak, K. A., et al., J. Org. Chem. 55, 3377 (1990); and Sato, F., et al., J. Org. Chem., 53, 5590 (1988)).

U.S. Pat. No. 4,873,360 to Johnson et al also describes another route to the cyclopentanoids, particularly the prostaglandins. This patent describes useful target PGs for the present invention.

The α-haloenones are disclosed for use in the synthesis of Rα-cyclopentenone intermediates capable of transition-metal catalyzed cross-coupling with the α-side-chain using a process described by the inventor and co-workers in Johnson, C. R., et al., Tetrahedron Lett., 33, 917 (1992).

OBJECTS

It is therefore an object of the present invention to provide a novel and highly efficient process for producing the Rα-cyclopentenones and then the Rα, Rω-cyclopentanoids. Further it is an object of the present invention to provide a method which is relatively simple and economical. These and other objects will become increasingly apparent by reference to the following description.

DESCRIPTION OF PREFERRED EMBODIMENTS

The present invention relates to a process for preparing a Rα-cyclopentenone which comprises reacting in a

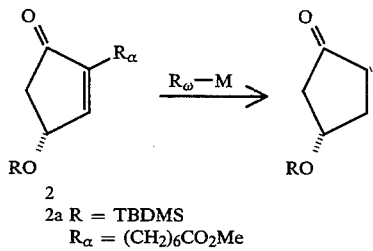

2a R = TBDMS
$R_α = (CH_2)_6CO_2Me$

1a R = TBDMS

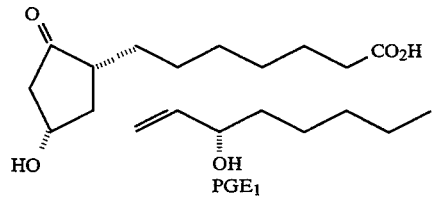

$PGE_1$

The one-pot three-component coupling synthesis Equation (1) is one of the most direct means of assembling reaction mixture at a temperature between about 0° and 100° C. an enone compound of the formula:

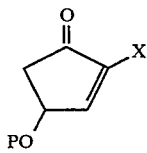

wherein P is a protecting group with an alkylborane of the formula

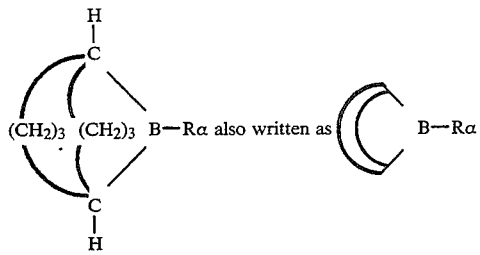

where Rα is an aliphatic group containing 3 to 20 carbon atoms and X is iodo or bromo in an organic solvent mixture containing a catalytic amount of a transition metal compound in the presence of a base and water to produce the Rα-cyclopentenone; and separating the Rα-cyclopentenone from the reaction mixture.

The present invention particularly relates to a process for preparing a Rα-cyclopentenone which comprises reacting in a reaction mixture at a temperature between about −25° and 50° C. an enone compound of the formula:

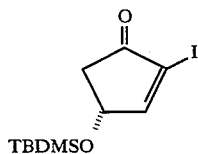

TBDMSO wherein TBDMSO is tert-butyldimethylsiloxy) with an alkylborane of the formula

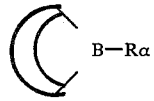

where Rα is an aliphatic group containing 3 to 20 carbon atoms and X is iodo or bromo in an organic solvent mixture containing a catalytic amount of a transition metal compound in the presence of a base and water to produce the Rα-cyclopentenone; and separating the Rα-cyclopentenone from the reaction mixture.

The Rα-cyclopentenone is used to produce a cyclopentanoid. Usually a Rω cuprate is reacted with the Rα-cyclopentenone to produce a protected compound of the formula

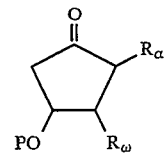

the PO group is converted to a hydroxyl group to produce the 4-hydroxycyclopentanoid. Rω is generally an aliphatic group.

Rα can be alkyl, alkenyl, alkynyl, ester, ketone and amide groups containing 3 to 20 carbon atoms which are substituted with various groups which do not interfere with the reaction, such as saturated and unsaturated rings including phenyl and heterocyclic groups (O,N, or S) containing 3 to 6 carbon atoms, to provide the Rα-cyclopentenone. Rα preferably is saturated and as follows:

—(CH$_2$)$_6$CO$_2$CH$_3$

Rω can be alkyl or alkenyl groups containing 1 to 12 carbon atoms including aryl and hydroxyl substituents in these groups. Rω is preferably an octyl group containing a hydroxyl group as follows:

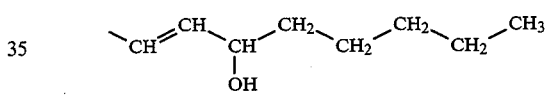

The PO group can be tert-butyldimethyl silyloxy, which is preferred, or R$_1$, R$_2$, R$_3$-SiO wherein R$_1$, R$_2$ and R$_3$ can be individually alkyl or aryl, allyl, aralkyl or acyl.

The preferred base is cesium carbonate. Tribasic potassium phosphate and barium hydroxide can also be used.

The preferred transition metal catalyst is palladium. The reaction is preferably catalyzed with a palladium salt complexed with ligands, particularly (diphenylphosphino)ferrocene (dppf) and, optionally, triphenylarsene (Ph$_3$As).

The overall approach was a two-step, three-component coupling synthesis in which the sidechains were installed in reverse fashion (Rα followed by Rω) to the traditional process as shown in Scheme I:

Scheme I

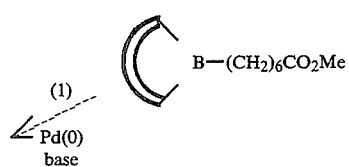

Scheme I

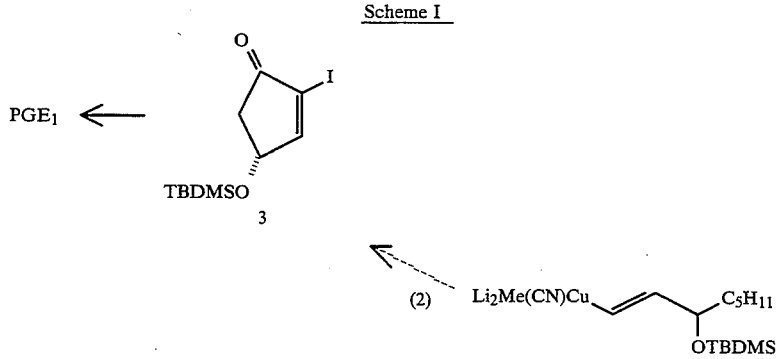

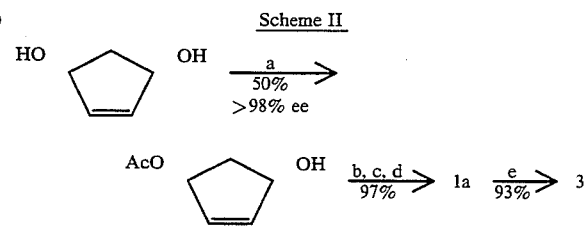

Using the coupling with 9-alkyl-9-BBN reagents, a general synthesis of Rα-enones from α-haloenones (bromo or iodo) was developed, The general chemistry developed by Suzuki et al and Miyaura et al for Pd(0)-catalyzed cross-coupling of alkylboranes with aryl or alkenyl halides was used (Miyaura, N,, et al,, M. J. Am, Chem, Soc, 111, 314–321 (1989); and Suzuki, A., et al., Pure & Appl. Chem., 63, 419 (1991)). The Suzuki reaction is particularly attractive in that the alkylborane reagents are easily prepared (in situ, if desired) and, in most cases, display little reactivity with other functionalities, In addition, Pd(0)-catalyzed coupling occurs under mildly basic conditions and is tolerant of a wide range of functionality (ketone, aldehyde, ester, nitrile, alcohol, and the like) making the overall process highly adept in the synthesis of delicate compounds such as PGs.

The reaction temperature in forming the Rα-cyclopentenoid is generally between about $-25°$ and $50°$ C. and preferably $25°$ to $30°$ C. The solvent for the reaction is water and an organic solvent. The preferred organic solvent is a mixture of dimethylformamide (DMF) and tetrahydrofuran (THF). Other solvents are 1,2-dimethoxyethane and N-methylpyrrolidinone.

A wide variety of Rα, Rω-cyclopentenoids can be produced from the Rα-cyclopentenones and the problems of electrophilic capture chemistry was avoided. The utility of this technique was demonstrated in the synthesis of natural PGE$_1$, methyl ester. The process is useful for the synthesis of many PG analogs in the same manner.

EXAMPLE 1

Yields are of chromatographically pure products. NMR spectra were recorded on a GE QE300, GE GN300 or Varian Gemini300 spectrometer with CDCl$_3$ as solvent and internal standard unless otherwise stated. Optical rotations were measured with a Perkin-Elmer Model 241 polarimeter. All air and/or moisture sensitive reactions were carried out under an atmosphere of argon or nitrogen in oven or flame dried glassware. THF was purified by distillation from benzophenone ketyl. Column chromatography was carried out with EM 230–400 mesh silica gel 60 and monitored by TLC analysis performed on glass plates precoated at 0.25 mm Whatman silica gel 60 A K6F (Whatman International, Maidstone, England), developed under UV and 10% phosphomolybdic acid (PMA) spray. 9-BBN, 6-heptenoic acid, and Ph$_3$As were obtained from the Aldich Chemical Company (Milwaukee, Wisc.) and used without further modification. PdCl$_2$(dppf (diphenylphosphino) ferrocene)) was prepared by the literature procedure (Hayashi, T., et al., J. Am. Chem. Soc., 106, 158 (1984)).

Although many syntheses of the enantiopure ring and lower sidechain components (Noyori, R., et al., J. Am. Chem. Soc., 110, 4718 (1988)) have been reported, newly developed chemistry on the use of the biocatalyst SP-435 was used (Johnson, C. R., Tetrahedron Lett., 33, 7287 (1992)). The enone 1a shown in Scheme II was prepared by SP-435-catalyzed asymmetrization of cis-1,4-cyclopentenediol (Johnson, C. R., et al, Tetrahedron Lett. 33, 7287 (1992)) followed by protecting group manipulation and oxidation as follows:

Scheme II $^a$(a) SP-435 (*Candida antarctica* lipase B) (Nova Nordick, Bagevaerd, Denmark), isopropenyl acetate, 50° C. (b) TBDMSCl, imidazole, DMF. (c) NaCN, MeOH. (d) PDC, CH$_2$Cl$_2$. (e) I$_2$ (1.8 eq), pyridine/CCl$_4$ (3:2).

(4R)-tert-Butyldimethylsiloxy-2-cyclopentenone (1a). This compound was prepared using the method described above. $(\alpha)^2$D = +51.7° (c 0.48, CHCl$_3$); $^1$H NMR (CDCl$_3$) δ 7.42 (dd, 1 H, J=5.4, 2.4 Hz), 6.13 (d, 1 H, J=5.4 Hz), 4.95 (ddd, 1 H, J=6.0, 2.4, 2.0 Hz), 2.66 (dd, 1 H, J=18.3, 6.0 Hz), 2.20 (dd, 1 H, J=18.3, 2.0 Hz), 0.87 (s, 9 H), 0.09 (s, 3 H) , 0.01 (s, 3 H); $^{13}$C NMR (CDCl$_3$) δ 206.5, 163.9, 134.5, 70.9, 45.0, 25.8, 8.2, −4.7; HRMS (EI) m/z 212.1230 (exact mass calcd for C$_{11}$H$_{20}$O$_2$Si 212.1232).

(4R)-2-Iodo-4-(tert-butyldimethylsiloxy)-2-cyclopentenone (3). α-Iodination of compound 1a was efficiently accomplished with iodine and pyridine (Johnson, C. R., et al., Tetrahedron Lett., 33, 917 (1992)) to give compound 3 (Scheme I) $(\alpha)^{22}$D+24.3 (c 0.60, CHCl$_3$); mp 38.5° C. in 93% yield.

Enone 1a (6.66 g, 31.34 mmol) in 20 mL pyridine/carbon tetrachloride (3:2) was cooled to 0° C. with an ice bath. With stirring, I$_2$ (14.32 g, 56.41 mmol) dissolved in 50 mL of pyr/CCl$_4$ was added via pipet and the ice bath removed. After 0.5 h stirring the dark solution was taken up in diethyl ether (350 mL) and washed consecutively with water (1×200 mL), 1 N HCl (2×300 mL), water (1×200 mL), 20% satd. Na$_2$S$_2$O$_3$(2×200 mL) and brine (1×100 mL). The ether layer was dried over MgSO$_4$ and filtered. Removal of solvent followed by chromatography (19:1 petroleum ether-ethyl acetate) gave the title compound (9.81 g, 93%) as a clear viscous oil which solidified upon standing. The product thus obtained was indefinitely stable when stored refrigerated in the dark, however, when exposed as a solution to room light for periods >2-4 h, significant decomposition can occur, $(\alpha)^{22}D = +24.3°$ (c 0.60, CHCl$_3$); mp 38.5° C.; $^1$H NMR (CDCl$_3$) δ 7.78 (d, 1 H, J=2.4 Hz), 4.94 (ddd, 1 H, J=6.0, 2.4, 2.1 Hz), 2.85 (dd, 1 H, J=18.3, 6.0 Hz), 2.33 (dd, 1 H, J=18.3, 2.1 Hz), 0.88 (s, 9 H), 0.11 (s, 3 H), 0.10 (s, 3 H); $^{13}$C NMR (CDCl$_3$) δ 200.3, 169.3, 105.1, 72.2, 42.5, 25.8, 18.2, −4.6; IR (neat) 2955, 2928, 2889, 2856, 1725, 1086, 907, 833, 780 cm$^{-1}$. Anal. Calcd for C$_{11}$H$_{19}$IO$_2$Si; C, 39.06; H, 5.66. Found: C, 38.96; H, 5.66.

Methyl 6-heptenoate required for hydroboration with 9-BBN-H to afford the α-sidechain was prepared by treatment of the commercially available carboxylic acid with diazomethane.

Methyl 7-(3(R)-tert-butyldimethylsiloxy-5-oxo-1-cyclopenten-1-yl) heptanoate (2a). To a flame-dried round-bottomed flask was added (0.631 g, 4.44 mmol) of methyl 6-heptenoate and 4 mL THF. The solution was cooled to 0° C. and a 0.5 M solution of 9-BBN (8.9 mL, 4.44 mmol) was added dropwise over 15 min. The solution was allowed to warm to room temperature and stirred an additional 4 h at which point approximately 50% of the THF was removed under reduced pressure. This formed the 9-(6-methoxycarbonyl)hexyl)-9-borabicyclic (3.3.1)nonane.

When the above operation was complete, in a separate flask, α-iodoenone 3 (1.00 g, 2.96 mmol) was dissolved/suspended along with Cs$_2$CO$_3$ (1.74 g, 5.34 mmol), PdCl$_2$(dppf) (0.065 g, 3 mol %), and Ph$_3$As (0.054 g, 10 mol %) in 10 mL DMF. H$_2$O (0.64 mL, 12 eq.) was then added with vigorous stirring followed by the THF solution of borane. The contents of the flask were stirred for 0.5-1.5 h at which point they were poured into water (100 mL) and extracted into diethyl ether (150 mL). The organics were washed with 1 N HCl (1×50 mL), 10% NH$_4$OH (1×50 mL), water (1×50 mL), brine (1×50 mL) and dried over MgSO$_4$. Filtration followed by removal of solvent and chromatography (15:1 petroleum ether-ethyl acetate) yielded the title compound 2a (0.803 g, 77%) as a clear oil $(\alpha)^{22}D = +21.8°$ (c 0.660, MeOH), lit. +22.8° (c 0.404, MeOH); $^1$H NMR (CDCl$_3$ δ6.98-7.00 (m, 1 H), 4.84-4.87 (m, 1 H), 3.61 (s, 3 H), 2.68 (dd, 1 H, J=18.3, 5.7 Hz), 2.25 (t, 2 H, J=7.5 Hz), 2.21 (dd, 1 H, J=18.3, 2.1 Hz) 2.11 (t, 2 H, J=7.5 Hz), 1.52-1.62 (m, 2 H), 1.39-1.49 (m, 2 H), 1.28 (m, 4 H), 0.86 (s, 9 H), 0.10 (s, 3 H), 0.06 (2, 3 H); $^{13}$C NMR (CDCl$_3$) δ 206.38, 174.30, 156.76, 147.21, 69.08, 51.53, 45.59, 34.09, 29.08, 28.90, 27.28, 25.88, 24.88, 24.46, 18.22, −4.57; IR (neat) 2935, 2857, 1738, 1717, 1255, 1081, 838, cm$^{-1}$; HRMS (EI) m/z 297.1524 (exact mass calcd for (minus tert-butyl) C$_{15}$H$_{25}$O$_4$Si 297.1522).

The Rω-enantiopure lower chain precursor was produced through an enzymatic resolution of commercially available 1-octyn-3-ol to give the (S)-acetate compound 5 in high ee (Sih, C. J., et al., J. Am. Chem. Soc., 97, 865 (1975); and Griengle, H., et al., Tetrahedron, 43, 5791 (1987)) as shown in Scheme III.

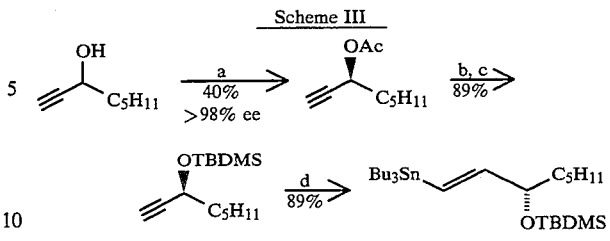

$^a$(a) SP-435, isopropenyl acetate, 25° C. (b) NaCN, MeOH. (c) TBDMSCl, imidazole, DMF. (d) Bu$_3$SnH, AIBN, 110° C. This material was easily transformed to the (E)-vinylstannane compound 6 by the literature route (Corey, E. J., et al., Tetrahedron Lett., 27, 2199 (1986)).

With the Compound 2a prepared, the traditional conjugate addition chemistry to obtain PGE$_1$, methyl ester as shown in Scheme IV was performed.

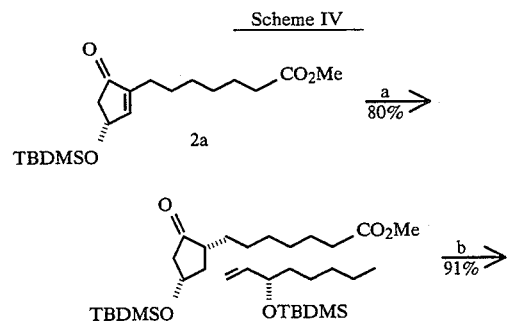

PGE$_1$, methyl ester
(a) i. vinyl cuprate derived from stannane 6, THF, −78° C.; ii. satd. aq. NH$_4$Cl, (b) HF, pyridine, CH$_3$CN.

For the Rα reactions, cesium carbonate (base) in a DMF/THF/water system gave the best results in the cross-coupling. The presence of water was necessary under all conditions tested in order for cross-coupling occur. This limitation is not normally observed with the Suzuki reaction. Other protic solvents such as methanol proved unsatisfactory.

In order to reduce the amount of β-hydride elimination from the transmetallated complex the use of the bis-(diphenylphosphino)ferrocene palladium(II) chloride (PdCl$_2$(dppf)) catalyst was preferred (Hayashi, T., et al., J. Am. Chem. Soc. 106, 158 (1984)). The co-ligand triphenylarsine was also used as its presence gave a higher turnover rate and cleaner reaction (Farina, V., et al., J. Am. Chem. Soc. 113, 9585 (1991)). Conjugate addition of the Rω-sidechain and deprotection were easily accomplished by literature procedures to give PGE$_1$, methyl ester in good yield (54% overall from enone 1a) (Scheme I) (Noyori, R., et al., J. Am. Chem. Soc., 110, 4718 (1988); Campbell, A. L., et al., J. Am. Chem. Soc., 110, 2641 (1988); and Myers, A. G., et al., J. Am. Chem. Soc., 115, 7021 (1993)). The reaction was conducted at 0° to 30° C. in an organic solvent, preferably tetrahydrofuran. Hydroflouric acid (HF) in pyridine with acetonitrile was used to remove the protecting TBDMSO groups.

The following Examples 2 to 7 in Table 1 shows various other Rα-cyclopentenones which were prepared by the process of the present invention.

TABLE 1

| Example | α-Iodoenone | Olefin | Method | Product | Yield (%) |
|---|---|---|---|---|---|
| 2 | TBDMSO-cyclopentenone-I | 1-Nonene | A, C | TBDMSO-cyclopentenone-$C_9H_{19}$ | 93 |
| 3 | | Allylbenzene | A, B | TBDMSO-cyclopentenone-CH$_2$CH$_2$Ph | 80, 42 |
| 4 | | CH$_2$=CH-CH(OTBS)-Et | A | TBDMSO-cyclopentenone-CH$_2$CH$_2$CH(OTBS)Et | 64 |
| 5 | | CH$_2$=CH-CH$_2$-CH$_2$-CH(O-CH$_2$CH$_2$CH$_2$-O) | A, C | TBDMSO-cyclopentenone-(CH$_2$)$_4$-CH(O-CH$_2$CH$_2$CH$_2$-O) | 91, 72 |
| 6 | | 2-bromostyrene | C | TBDMSO-cyclopentenone-CH$_2$CH$_2$-(2-Br-C$_6$H$_4$) | 42 |
| 7 | | CH$_2$=CH-(CH$_2$)$_3$-CO$_2$Me | A, B, C | TBDMSO-cyclopentenone-(CH$_2$)$_5$-CO$_2$Me | 69, 75, 94 |

Method A: PdCl$_2$(dppf) (3 mol %), Ph$_3$As (6 mol %), 2M K$_3$PO$_4$ (1.5 eq), DMF, R.T.
Method B: PdCl$_2$(dppf) (3 mol %), Ph$_3$As (6 mol %), Ba(OH)$_2$8H$_2$O (1.5 eq), DMF, R.T.
Method C: PdCl$_2$(dppf) (3 mol %), Ph$_3$As (6 mol %), Cs$_2$CO$_3$ (1.5 eq), H$_2$O (12 eq.), DMF, R.T.
RT — Room Temperature.

It is intended that the foregoing description be only illustrative of the present invention and that the present invention be limited only to the hereinafter appended claims.

We claim:

1. A process for preparing a Rα-cyclopentenone which comprises:
   (a) reacting in a reaction mixture at a temperature between about −25° and 50° C. an enone compound of the formula:

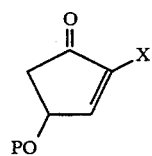

wherein P is a protecting group with an alkylborane of the formula

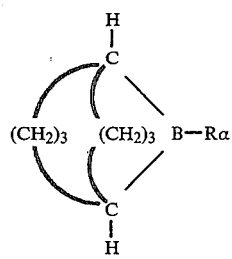

where Rα is an aliphatic group containing 3 to 20 carbon atoms and X is iodo or bromo in an organic solvent mixture containing a catalytic amount of a transition metal compound in the presence of a base and water to produce the Rα-cyclopentenone; and (b) separating the Rα-cyclopentenone from the reaction mixture.

2. A process for preparing a Rα-cyclopentenone which comprises:

(a) reacting in a reaction mixture at a temperature between about −25° and 50° C. an alpha-enone compound of the formula:

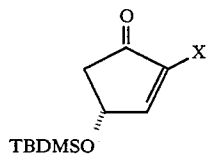

wherein TBDMSO is tert-butyldimethylsiloxy with an alkylborane of the formula

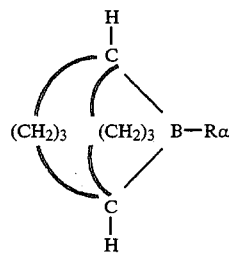

where Rα is an aliphatic group containing 3 to 20 carbon atoms and X is iodo or bromo in an organic solvent mixture containing a catalytic amount of a transition metal compound in the presence of a base and water to produce the Rα-cyclopentenone; and (b) separating the Rα-cyclopentenone from the reaction mixture.

3. The process of claim 2 wherein the base is selected from the group consisting of cesium carbonate, tribasic potassium phosphate and barium hydroxide.

4. The process of claim 3 wherein the transition metal compound is a palladium complex.

5. The process of claim 4 wherein the palladium complex is a complex of (diphenylphosphino) ferrocene and a palladium (II) salt.

6. The process of claim 5 wherein the salt is palladium chloride.

7. The process of claim 2 wherein the organic solvent is a mixture of dimethylformamide and tetrahydrofuran.

8. The process of claim 5 wherein the palladium complex includes triphenylarsine.

9. The process of claim 8 wherein the alkylborane is a heptylborane.

10. The process of claim 2 wherein alkyl contains 7 carbon atoms.

11. The process of claim 2 wherein a catalytic amount of triphenylarsine and (diphenylphosphino) ferrocene is included in the reaction mixture.

12. The process of claim 4 wherein the alkylborane is 9-(6(methoxycarbonyl)hexyl)-9-borabicyclo (3.3.1) nonane, the organic solvent is a mixture of dimethylformamide and tetrahydrofuran, the palladium complex is palladium chloride complexed with (diphenylphosphino) ferrocene and triphenylarsine and X is iodo and the temperature is between about 25° and 30°.

* * * * *